United States Patent
Chai

(10) Patent No.: US 9,358,757 B2
(45) Date of Patent: Jun. 7, 2016

(54) SMART MULTI-LAYER COMPOSITES

(71) Applicant: Kyung Nam Chai, Seongnam-si (KR)

(72) Inventor: Kyung Nam Chai, Seongnam-si (KR)

( * ) Notice: Subject to any disclaimer, the term of this patent is extended or adjusted under 35 U.S.C. 154(b) by 133 days.

(21) Appl. No.: 14/228,805

(22) Filed: Mar. 28, 2014

(65) Prior Publication Data

US 2014/0292357 A1   Oct. 2, 2014

(30) Foreign Application Priority Data

Apr. 1, 2013   (KR) ........................ 10-2013-0035156

(51) Int. Cl.

| | |
|---|---|
| *G01R 27/08* | (2006.01) |
| *B32B 7/12* | (2006.01) |
| *G01N 27/20* | (2006.01) |
| *G01M 5/00* | (2006.01) |
| *B32B 9/00* | (2006.01) |
| *B32B 9/04* | (2006.01) |
| *B32B 15/08* | (2006.01) |
| *B32B 15/12* | (2006.01) |
| *B32B 15/14* | (2006.01) |
| *B32B 15/20* | (2006.01) |
| *B32B 27/30* | (2006.01) |
| *B32B 27/38* | (2006.01) |
| *G01N 3/06* | (2006.01) |

(52) U.S. Cl.
CPC . *B32B 7/12* (2013.01); *B32B 9/007* (2013.01); *B32B 9/041* (2013.01); *B32B 9/045* (2013.01); *B32B 9/047* (2013.01); *B32B 15/08* (2013.01); *B32B 15/12* (2013.01); *B32B 15/14* (2013.01); *B32B 15/20* (2013.01); *B32B 27/30* (2013.01); *B32B 27/38* (2013.01); *G01M 5/0033* (2013.01); *G01M 5/0083* (2013.01); *G01N 27/205* (2013.01); *B32B 2255/26* (2013.01); *B32B 2260/021* (2013.01); *B32B 2260/046* (2013.01); *B32B 2262/101* (2013.01); *B32B 2262/103* (2013.01); *B32B 2262/105* (2013.01); *B32B 2262/106* (2013.01); *B32B 2419/00* (2013.01); *B32B 2605/00* (2013.01); *G01N 3/066* (2013.01); *Y02B 10/30* (2013.01); *Y10T 428/30* (2015.01)

(58) Field of Classification Search
CPC ........ G01N 27/06; G01N 27/02; G01N 27/41
USPC .......................................... 324/693, 691, 639
See application file for complete search history.

(56) References Cited

U.S. PATENT DOCUMENTS

| 5,039,571 A * | 8/1991 | Vogelesang ............. B32B 15/08 428/213 |
| 8,269,401 B1 * | 9/2012 | Kim ...................... H01L 41/113 310/339 |
| 2009/0047471 A1 * | 2/2009 | Kellenberger .......... B29C 70/12 428/138 |

(Continued)

FOREIGN PATENT DOCUMENTS

| JP | 2010-508416 A | 3/2010 |
| KR | 10-2012-0111607 A | 10/2012 |

*Primary Examiner* — Tung X Nguyen
*Assistant Examiner* — Dominic Hawkins
(74) *Attorney, Agent, or Firm* — Pearne & Gordon LLP

(57) ABSTRACT

A smart multi-layer composite is disclosed. The smart multi-layer composite includes a plurality of layers stacked in sequence; and a graphene layer interposed between the plurality of layers.

2 Claims, 3 Drawing Sheets

(56) References Cited

U.S. PATENT DOCUMENTS

| | | | |
|---|---|---|---|
| 2009/0050814 A1* | 2/2009 | Seefeldt | H01L 31/117 250/370.07 |
| 2009/0294022 A1* | 12/2009 | Hayes | G01N 27/20 156/94 |
| 2011/0285999 A1* | 11/2011 | Kim | G01N 21/552 356/445 |
| 2012/0080662 A1* | 4/2012 | Saito | H01L 21/28556 257/29 |
| 2012/0128983 A1* | 5/2012 | Yoon | B82Y 30/00 428/408 |
| 2012/0181501 A1* | 7/2012 | Sung | C01B 31/0446 257/9 |
| 2014/0147622 A1* | 5/2014 | Preisler | B29C 43/00 428/116 |

* cited by examiner

SMART MULTI-LAYER COMPOSITES

CROSS-REFERENCE TO RELATED APPLICATION

This application claims the benefit of Korean Patent Application No. 10-2013-0035156 filed on Apr. 1, 2013, the entire disclosures of which are incorporated herein by reference.

FIELD OF THE INVENTION

The present disclosure relates to smart multi-layer composite.

BACKGROUND OF THE INVENTION

A composite is a material produced by mixing or combining two or more independent components or phases in various ways. Each of the components has a content at a significant level, i.e. 5% or more. It this case, the components have different properties. Thus, the composite as a mixture of the components has properties different from those of each component. That is, the composite is a combination of chemically independent a plurality of phases at a microscopic level, and it is very important to identify properties of each phase.

The components of the composite include a matrix and a stiffener. The matrix is a component in the form of a continuum and takes up a considerable part of the total volume of the composite and determines a macroscopic shape of the composite. Further, the stiffener dominates strength and stiffness of the composite and the stiffener's form is maintained by the matrix. A representative stiffener is fiber.

In most cases, a composite comprised of such components is lighter, stronger and less easily transformed than a matrix due to an effect of a stiffener. It can be seen that a mechanical property of the composite is determined depending on a function of shapes and contents of the matrix and the stiffener.

Methods to reinforce a material in the form of a composite are roughly two methods: a fibrous method and a particulate method. The fibrous method uses continuous fiber or discontinuous fiber having a very long length as compared with a cross-sectional dimension. The particulate method uses particles with similar dimensions in all directions. By way of example, particles having a regular shape, such as a circle, a hexahedron, and the like, or an irregular shape may be used in the particulate method.

A composite may be formed in a single layer or a plurality of layers. Multi-layer composites include laminates, hybrid composites, and the like. The laminates have a structure of the plurality of layers (plies or laminas) stacked in a specific sequence. Further, the hybrid composites are composites produced from many kinds of fibers and can be produced by layering, or mixing or combining, for example, glass fibers and carbon fibers.

However, such a composite has complicated damage mechanisms depending on repeated loadings and the number of repeated loadings as compared with a metal material, and it is difficult to observe such complicated damage from the outside. By way of example, in a composite, complicated damage such as fiber breakage, matrix cracking, ply delamination, fiber/metal delamination, plastic deformation, and the like may occur. Further, a composite is very vulnerable to an impulsive load, and, thus, such damage frequently occurs. Furthermore, if damage occurs from the inside, its load supporting capacity is sharply decreased.

Such a composite is contained in a structure, bodywork, a load supporting body, e.g. cars, railroad cars, airplanes, ships, buildings, wind turbine blades, and the like, it is not easy to recognize whether or not internal damage occurs.

BRIEF SUMMARY OF THE INVENTION

In view of the foregoing, the present disclosure provides a smart multi-layer composite that enables easy diagnosis of internal damage occurring during use without an additional strain sensor.

In accordance with a first aspect of the present disclosure, there is provided a smart multi-layer composite, including a plurality of layers stacked in sequence; and a grapheme layer interposed between the pluralities of layers.

In accordance with a second aspect of the present disclosure, there is provided a method of diagnosing internal damage of a target object, including monitoring a change in resistance of a smart multi-layer composite contained in the target object; and if a change in resistance is detected, recognizing internal damage of the target object and identifying a position where the change in resistance occurs.

In accordance with the present disclosure, since a smart multi-layer composite contains a graphene layer, it is possible to easily diagnose internal damage occurring during use by using a piezo-resistive characteristic of the graphene layer without an additional strain sensor.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which.

DETAILED DESCRIPTION OF THE INVENTION

Figure 1A:
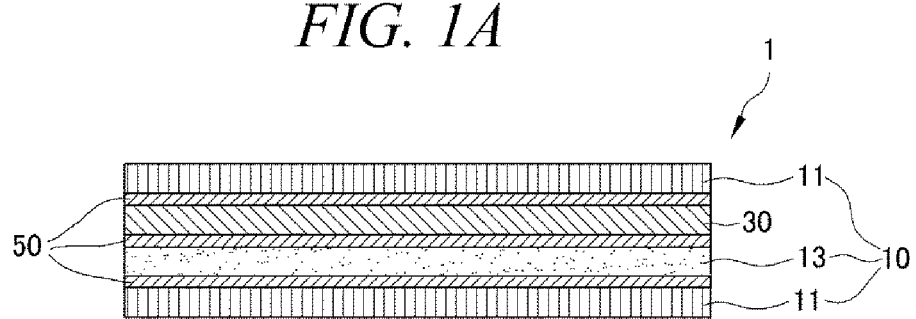
FIGS. 1A and 1B are cross-sectional views of a smart multi-layer composite in accordance with an illustrative embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for simplicity of explanation, and like reference numerals denote like parts through the whole document.

Through the whole document, the term "on" that is used to designate a position of one element with respect to another element includes both a case that the one element is adjacent to the another element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

For reference, the terms (upper side, lower side, and the like) related to directions or positions in the explanations of the embodiments of the present disclosure are based on arrangement of respective components as shown in the drawings. By way of example, a top side and a bottom side in FIGS. 1A and 1B may be an upper side and a lower side. However, in various practical applications of the embodiments of the present disclosure, the upper side and the lower side may be set on the contrary to this or in various different ways.

Hereinafter, illustrative embodiments of the present disclosure will be explained in detail with reference to the accompanying drawings.

A smart multi-layer composite 1 (hereinafter, referred to as "the present smart multi-layer composite") in accordance with an illustrative embodiment of the present disclosure will be explained first.

The present smart multi-layer composite 1 includes a plurality of layers 10.

Referring to FIGS. 1A, 1B and FIGS. 2A, 2B, the multiple layers 10 are stacked in sequence.

A composite is a material combined by mixing, stacking, or arranging two or more independent components or phases and has properties which cannot be expected from each of the components or phases. Multi-layer composites composed of the plurality of layers include laminates, hybrid composites, and the like.

At least one of the pluralities of layers 10 may include a matrix and a stiffener arranged within the matrix.

A laminate is a material manufactured by forming one or more flat plates (plies or laminas) by adding a stiffener (for example, fiber) into a matrix, and stacking the flat plates in a specific sequence (for example, in a sequence so as to arrange fibers in different directions).

Herein, the matrix is a component in the form of a continuum and takes up a considerable part of the total volume of the composite and determines a macroscopic shape of the composite. Further, the stiffener dominates strength and stiffness of the composite and the stiffener's form is maintained by the matrix. The stiffener may be formed in fiber or thread or may be formed in fine dispersed particles having a plate shape or a ball shape.

By way of example, if the present smart multi-layer composite 1 contains such a laminate, at least one of the plurality of layers 10 may be a lamina or a ply.

Further, at least one of the plurality of layers 10 may be a blend of the plurality of stiffeners.

A hybrid composite is a material manufactured by blending many kinds of stiffeners (for example, fibers). Herein, the blending means combination of many kinds of stiffeners by layering, mixing or combining.

By way of example, if the present smart multi-layer composite 1 contains such a hybrid composite, at least one of the plurality of layers 10 may be a combination of two or more stiffeners.

Herein, at least one of the plurality of stiffeners may be a fiber stiffener.

Desirably, the fiber stiffener may have a high strength. By way of example, a material of the fiber stiffener may be metal, glass, carbon, ceramic, (artificial and natural) organic matters.

Referring to FIGS. 1A, 1B and FIGS. 2A, 2B, outermost layers 10 of the plurality of layers 10 may be aluminum sheets 11.

Figure 1B:
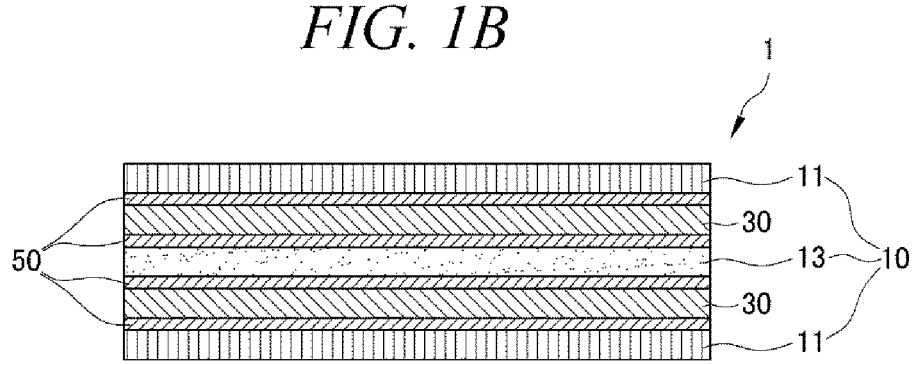
Figure 2A:
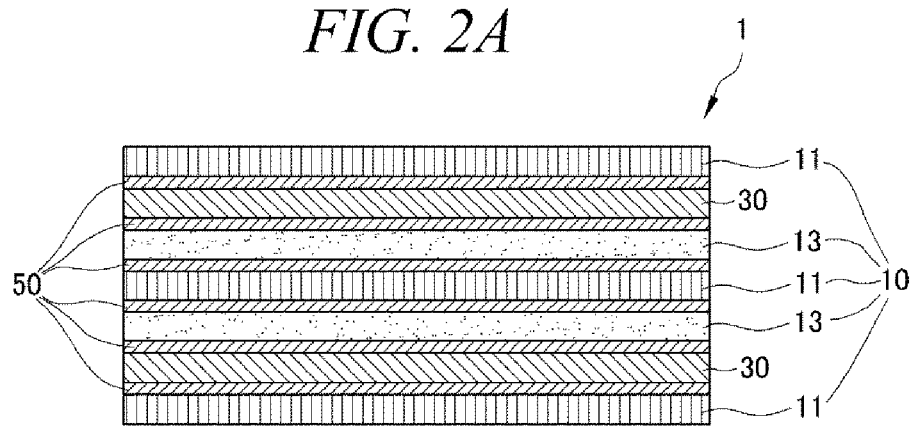
FIGS. 2A and 2B are cross-sectional views of a smart multi-layer composite in accordance with another illustrative embodiment of the present disclosure.
Figure 2B:
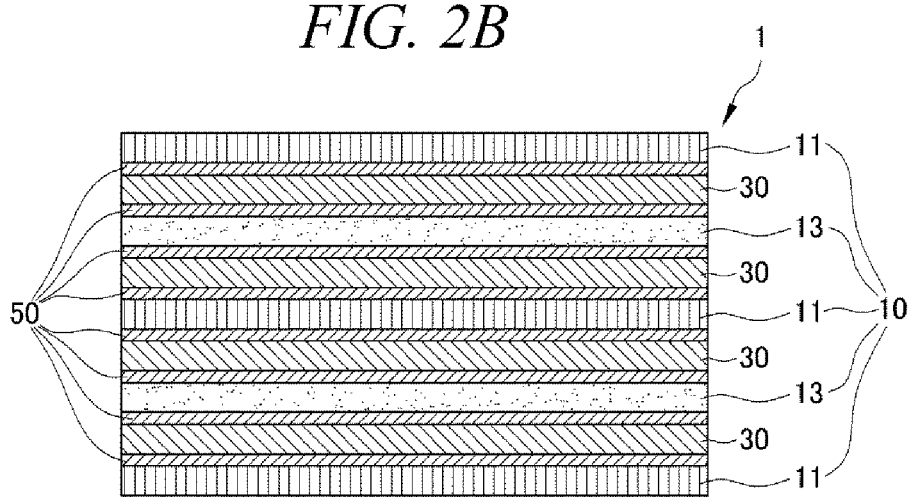

The aluminum sheets 11 may be arranged at outermost positions as depicted in FIGS. 1A and 1B, or may be arranged at outermost positions and between outermost layers 10 as depicted in FIGS. 2A and 2B.

Herein, the aluminum sheets 11 may be made of pure aluminum or made of an aluminum alloy containing other components.

Further, referring to FIGS. 1A, 1B and FIGS. 2A, 2B, at least one of the layers 10 between the aluminum sheets 11 may be a glass fiber prepreg layer 13.

Prepreg as an intermediate base material of a fibrous composite is produced by preliminarily impregnating a matrix resin in a reinforced fiber. Glass fiber prepreg is a reinforced fiber using a fiber made of glass.

The glass fiber prepreg layer 13 may be one of the plurality of layers 10 as depicted in FIGS. 1A and 1B or may be a plurality of layers as depicted in FIGS. 2A and 2B.

The present smart multi-layer composite 1 contains a graphene layer 30.

The graphene layer 30 is interposed between the pluralities of layers 10.

Referring to FIGS. 1A, 1B and FIGS. 2A, 2B, the graphene layer 30 may be inserted, for example, between the aluminum sheet 11 and the glass fiber prepreg layer 13.

A composite is mainly used in a structure, bodywork, and a load supporting body, e.g. cars, railroad cars, airplanes, ships, buildings, wind turbine blades, and the like. However, the composite is very vulnerable to an impulsive load, and, thus, damage frequently occurs, and if damage occurs, its load supporting capacity is sharply decreased. Therefore, safety of a target object containing such a material cannot be guaranteed.

Accordingly, in order to improve safety of a target object containing a composite, it is necessary to recognize and repair damage occurring in the composite as early as possible. However, the composite has complicated damage mechanisms (for example, matrix cracking, ply delamination, separation between a matrix and a stiffener, plastic deformation, and the like), and it is difficult to observe such damage from the outside.

In this regard, since the present smart multi-layer composite 1 contains the graphene layer 30, it is possible to easily recognize internal damage, which cannot be observed from the outside, without an additional sensor. In this case, the graphene layer 30 detects internal damage. Details thereof will be described later.

One or more graphene layers 30 may be interposed between the plurality of layers 10. By way of example, as depicted in FIG. 1A, only one graphene layer 30 may be interposed between the plurality of layers 10. Otherwise, as depicted in FIG. 2A, one or more graphene layers 30 may be interposed between the plurality of layers 10. In this case, a part where the graphene layer 30 is interposed may be a part to be deformed first by, if any, external shocks.

Otherwise, as necessary, the graphene layer 30 may be interposed between the respective layers 10 as depicted in FIG. 1B and FIG. 2B.

The graphene layer 30 may behave as one body with the adjacent layer 10 of the plurality of layers 10.

Therefore, if a deformation zone is formed on the adjacent layer 10 as described later, there may be a change in resistance at a zone corresponding thereto on the graphene layer 30.

By way of example, the graphene layer 30 may be bonded to the adjacent layer 10 by an adhesive layer 50 to be described later and fixed thereto as one body.

A resistance of the graphene layer 30 may be changed in response to a stress applied.

Since graphene has a piezo-resistive characteristic, when an external force is applied to the graphene, a balance of crystallization is changed, thus, a resistance is changed.

In the present smart multi-layer composite 1, the graphene layer 30 serves as a strain sensor by using such a piezo-resistive characteristic of graphene. Therefore, it is possible to recognize internal damage of the composite without an additional sensor.

That is, if damage such as stiffener breakage, matrix cracking, ply delamination, separation between a matrix and a stiffener, plastic deformation, and the like occurs at any one layer 10 of the present smart multi-layer composite 1, a stress is transmitted to the graphene layer 30 due to such damage and a resistance of the graphene layer 30 is changed. Therefore, when a resistance of the graphene layer 30 is changed, even if whether or not damage occurs cannot be observed from the outside, it is possible to recognize that the inside of the present smart multi-layer composite 1 is damaged.

Further, graphene has a tensile strength of about 120 GPa to about 130 GPa, which means that the graphene has a mechanical strength about 200 times greater than steel. Therefore, since the graphene layer 30 is contained in the present smart multi-layer composite 1, the present smart multi-layer composite 1 can have a further improved mechanical strength.

If a deformation zone is formed by an external force on one of the plurality of layers 10 adjacent to the graphene layer 30, a resistance of the graphene layer 30's part adjacent to the deformation zone may be changed.

To be more specific, referring to FIGS. 1A, 1B and FIGS. 2A, 2B, if a deformation zone is formed on the layer 10 bonded to the graphene layer 30 by the adhesive layer 50, a balance of crystallization may be changed at the graphene layer 30's part adjacent to the deformation zone and a resistance of the graphene layer 30 may be changed.

In this case, by detecting the part with a changed resistance on the graphene layer 30, it is possible to detect a position of internal damage in the present smart multi-layer composite 1. Therefore, it is possible to more rapidly find a position of internal damage in the present smart multi-layer composite 1, and it is possible to efficiently perform a repair by replacing a damaged part of a replaceable component or reinforcing a damaged part instead of replacing the whole target object.

Further, by detecting a changed resistance ratio of the graphene layer 30, it is possible to recognize an overall deformation rate of the present smart multi-layer composite 1. Accordingly, a damage level of the composite can be recognized. Therefore, it is possible to efficiently and appropriately handle damage by repairing only a damaged part in the case of a low damage level and by replacing a damaged part in the case of a high damage level.

The present smart multi-layer composite 1 may contain the adhesive layer 50 that bonds the layers 10 different from each other or bonds the layers 10 to the graphene layer 30.

Referring to FIGS. 1A, 1B and FIGS. 2A, 2B, the adhesive layer 50 can bond the aluminum sheet 11 to the graphene layer 30 or the glass fiber prepreg layer 13 to the graphene layer 30.

Otherwise, although not illustrated in the drawings, the adhesive layer 50 can bond the aluminum sheets 11 different from each other or bond the layers 10 different from each other such as the aluminum sheet 11 and the glass fiber prepreg layer 13.

By way of example, the adhesive layer 50 may be a typically used epoxy resin, acryl resin, or the like.

Hereinafter, there will be explained a method of diagnosing internal damage of a target object (hereinafter, referred to as "the present method of diagnosing internal damage of a target object) in accordance with an illustrative embodiment of the present disclosure. The same or similar components of the smart multi-layer composite 1 as explained in the above-described illustrative embodiment of the present disclosure will be assigned same reference numerals, and redundant explanations thereof will be briefly provided or omitted.

Figure 3:
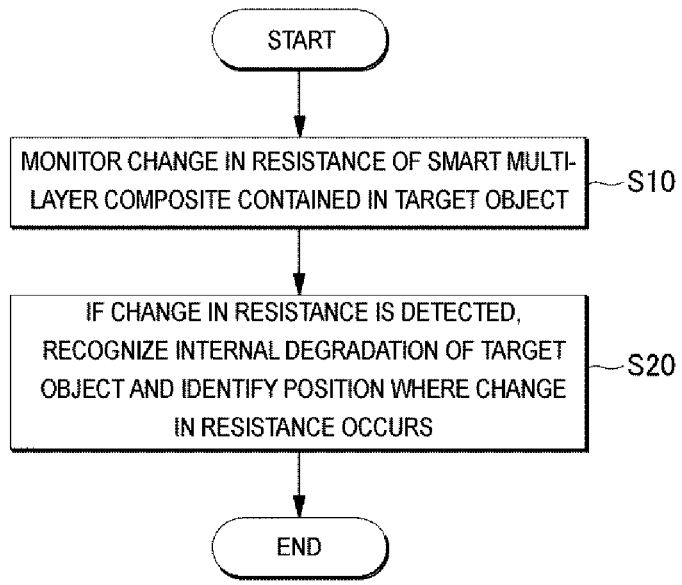
FIG. 3 is a flow chart illustrating a method of diagnosing internal damage of a target object in accordance with an illustrative embodiment of the present disclosure.

FIG. 3 is a flow chart for explaining the present method of diagnosing internal damage of a target object in accordance with an illustrative embodiment of the present disclosure.

The present method of diagnosing internal damage of a target object may comprise monitoring a change in resistance of the present smart multi-layer composite 1 contained in the target object (S10).

Herein, the target object may be, but not limited to, a structure, bodywork, and a load supporting body, e.g. cars, railroad cars, airplanes, ships, buildings, wind turbine blades, and the like, containing the smart multi-layer composite 1, and may include any target object of which internal damage needs to be detected for guarantee of safety.

By way of example, a current or a voltage is applied to the smart multi-layer composite 1 to monitor whether or not there is a change in current or voltage. Thus, it can be seen whether or not there is a change in resistance.

In the monitoring a change in resistance of the present smart multi-layer composite 1 (S10), a change in resistance may be caused by a change in resistance of the graphene layer 30 occurring in response to a stress applied.

As explained above, since graphene has a piezo-resistive characteristic, when an external force is applied to the graphene, a balance of crystallization may be changed and a resistance may be changed. In the present smart multi-layer composite 1, the graphene layer 30 serves as a strain sensor by using such a piezo-resistive characteristic of graphene. Therefore, it is possible to recognize internal damage of the composite without an additional sensor.

The present method of diagnosing internal damage of a target object may comprise, if a change in resistance is detected, recognizing internal damage of the target object and identifying a position where the change in resistance occurs (S20).

As explained above, a composite is mainly used in a structure, bodywork, and a load supporting body, e.g. cars, railroad cars, airplanes, ships, buildings, wind turbine blades, and the like. However, the composite is very vulnerable to an impulsive load, and if damage occurs, its load supporting capacity is sharply decreased and it is not easy to recognize whether or not internal damage occurs. Therefore, safety of a target object containing such a material cannot be guaranteed.

Accordingly, if any one layer 10 contained in the smart multi-layer composite 1 is damaged, a stress is transmitted to the graphene layer 30 due to such damage, and a change in resistance of the graphene layer 30 is detected. Thus, it is possible to recognize that the inside of the smart multi-layer composite 1 contained in the target object is damaged, so that safety of the target object containing the composite can be improved.

Further, by detecting a part with a changed resistance on the graphene layer 30, it is possible to detect a position of internal damage in the smart multi-layer composite 1 contained in the target object. Therefore, it is possible to more rapidly find a position of internal damage in the smart multi-layer composite 1 contained in the target object, and it is possible to efficiently perform a repair by finding and repairing only a damaged part instead of replacing the target object itself.

The present method of diagnosing internal damage of a target object may comprise, after the recognizing internal damage of the target object and the identifying a position where the change in resistance occurs (S20), detecting a deformation rate of the position where the change in resistance occurs by using the change in resistance.

By detecting a changed resistance ratio of the graphene layer 30, it is possible to recognize a deformation rate of the smart multi-layer composite 1 contained in the target object. Accordingly, a damage level of the target object can be recognized. Therefore, it is possible to efficiently and appropriately handle damage by repairing only a damaged part in the case of a low damage level and by replacing a damaged part in the case of a high damage level.

A composite is very vulnerable to an impulsive load, and if damage occurs, its load supporting capacity is sharply decreased. Thus, it is necessary to rapidly detect damage in the composite, but it is difficult to observe internal damage from the outside. However, according to the present smart multi-layer composite 1 and the present method of diagnosing internal damage of a target object, it is possible to easily and rapidly recognize internal damage by using a change in resistance of the graphene layer 30 without an additional sensor to detect internal damage. Therefore, safety of a target object containing the present smart multi-layer composite 1, such as cars, airplanes, ships, buildings, wind turbine blades, and the like, can be further improved.

Further, according to the present smart multi-layer composite 1 and the present method of diagnosing internal damage of a target object, by identifying a position where a change in resistance occurs in the graphene layer 30, a position of damage within the target object containing the present smart multi-layer composite 1 can be identified. Therefore, it is possible to rapidly find the position of damage and also possible to efficiently perform a repair by repairing only a damaged part instead of replacing the whole target object.

Furthermore, according to the present smart multi-layer composite 1 and the present method of diagnosing internal damage of a target object, by detecting a changed resistance ratio of the graphene layer 30, it is possible to detect a deformation rate of the smart multi-layer composite 1. Accordingly, by recognizing a damage level of the composite, it is possible to appropriately handle damage by repairing or replacing a damaged part depending on damage level.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A method of diagnosing internal damage of a target object containing a smart multi-layer composite comprising: a plurality of layers stacked in sequence; and a graphene layer interposed between the plurality of layers, the method comprising:
    monitoring a change in resistance of a smart multi-layer composite contained in the target object; and
    if the change in resistance of the smart multi-layer composite is detected, recognizing internal damage of the target object and identifying a position where the change in resistance occurs,
    after the recognizing internal damage of the target object and the identifying a position where the change in resistance occurs,
    detecting a deformation rate of the position by using the change in resistance.

2. A method of diagnosing internal damage of a target object containing a smart multi-layer composite comprising: a plurality of layers stacked in sequence; and a graphene layer interposed between the plurality of layers, the method comprising:
    monitoring a change in resistance of a smart multi-layer composite contained in the target object; and
    if the change in resistance of the smart multi-layer composite is detected, recognizing internal damage of the target object and identifying a position where the change in resistance occurs,
    wherein in the monitoring a change in resistance of the smart multi-layer composite,
    the change in resistance is caused by a change in resistance of the graphene layer occurring in response to a stress applied.

* * * * *